United States Patent
Michell

Patent Number: 5,950,623
Date of Patent: Sep. 14, 1999

[54] ADJUSTABLE PRESSURE LIMITING VALVE FOR ANESTHESIA BREATHING CIRCUIT

[75] Inventor: Brian C. Michell, Madison, Wis.

[73] Assignee: Ohmeda Inc., Liberty Corner, N.J.

[21] Appl. No.: 09/036,716

[22] Filed: Mar. 6, 1998

Related U.S. Application Data

[60] Provisional application No. 60/062,239, Oct. 16, 1997.
[51] Int. Cl.$^6$ .................................................. A62B 18/02
[52] U.S. Cl. ............................... 128/205.24; 128/205.12; 137/530
[58] Field of Search ...................... 137/530, 538, 137/524, 540; 128/205.24, 205.17, 205.12, 204.28, 205.14

[56] References Cited

U.S. PATENT DOCUMENTS

| | | |
|---|---|---|
| 2,315,775 | 4/1943 | D'Arcey . |
| 2,616,442 | 11/1952 | Holmes . |
| 3,370,827 | 2/1968 | Stehlin . |
| 3,576,194 | 4/1971 | Christensen . |
| 4,180,066 | 12/1979 | Millicken et al. .................. 128/205.24 |
| 4,545,405 | 10/1985 | LaBelle ................................... 137/524 |
| 5,419,530 | 5/1995 | Kumar . |
| 5,566,669 | 10/1996 | Komesaroff ......................... 128/205.12 |

*Primary Examiner*—John G. Weiss
*Assistant Examiner*—Charles W. Anderson
*Attorney, Agent, or Firm*—Andrus, Sceales, Starke & Sawall

[57] ABSTRACT

An adjustable pressure limiting valve having a non-linear biasing means. The valve has a movable valve member that can be moved to an open position by a predetermined pressure and a closed position on a valve seat. A rotating control knob is rotated by the user to adjust the bias acting against the movable valve member toward the closed position to, in turn, set the pressure at which the valve opens. A rotating cylindrical drum rotates along with the control knob and has a helical groove formed in its exterior and a pair of fixed pins that ride in the helical groove. When the cylindrical drum is rotated, the fixed pins riding in the helical grove cause the cylindrical drum to move along its longitudinal axis to compress or decompress a spring acting against the movable valve member. The pitch of the helical groove is designed so as to create a non-linear relationship between the rotational movement of the control knob and the longitudinal movement of the cylindrical drum.

8 Claims, 2 Drawing Sheets

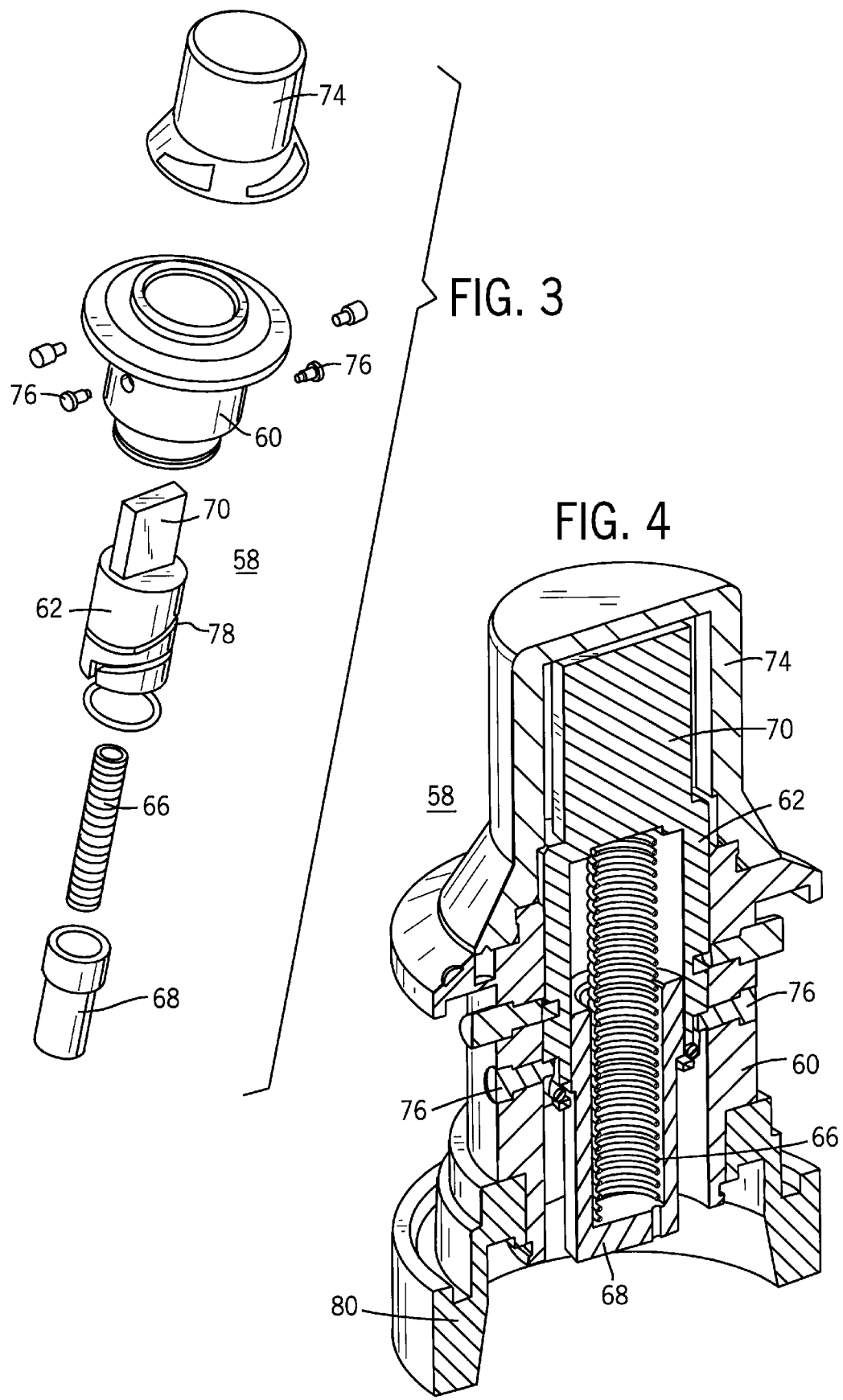

ADJUSTABLE PRESSURE LIMITING VALVE FOR ANESTHESIA BREATHING CIRCUIT

RELATED APPLICATIONS

This application is based upon Provisional Patent Application Ser. No. 60/062,239 filed Oct. 16, 1997.

BACKGROUND

The present invention relates to anesthesia patient breathing circuits and, more particularly, to a component of a breathing circuit that allows the relief of a selected maximum pressure in the breathing system.

Patient breathing circuits are utilized to convey gasses containing an anesthetic vapor to a patient to carry out the anesthetizing of that patient. In general, there are a variety of circuits and one particular circuit may be selected for use depending on the particular operation or upon the preference of the anesthesiologist. The overall purpose, however, is to convey those gases from an anesthesia machine where the proper combination of gases are mixed to deliver that mixed gas to the patient.

Accordingly, the components of such patent breathing circuit may include an absorber to rid the recirculating gases within the patient circuit of a $CO_2$ to prevent a $CO_2$ build-up, various check valves that insure the flow of gas within the patient circuit is in the proper direction, and also a pressure relief valve that vents the patient breathing circuit when the pressure within the circuit reaches a predetermined point so that the patient is not subjected to any excessive pressure. In its use, the pressure relief valve is referred to as an adjustable pressure limiting (APL) valve and is adjustable by the user so that differing maximum pressures are allowed in the patient breathing system during an operation and can be determined by the user.

In conventional valves, the APL valve comprises a simple movable valve member that is seated on a valve seat and which is held against that seat by means of an adjustable force, typical of which is a spring force that is adjustable and which acts against the motion of the movable valve member toward its open position. Thus, by simple adjustment of the spring force acting on the movable valve member, the user can select and change the force required to open that valve and, therefore, adjust the pressure required within the patient breathing circuit to open the valve to vent the patient breathing circuit.

One problem with such valves, however, is that the use of such springs to control a force against the opening of the movable member is that the spring exerts a linear, or near linear, characteristic as the spring is adjusted to change that force. That is, as the user normally rotates the control knob that is threaded to the valve base, the movement of the rotating control knob moves one end of a spring so that the spring is lengthened or shortened to alter the force of the spring against the movable valve member and the opening pressure is thus adjusted. Since it is nearly a linear relationship, a certain rotation of the control knob makes a finite, known change in the spring force generally throughout the range of travel of the rotatable knob.

Accordingly, there is a relatively uniform adjustment of the spring force with movement of the rotatable knob but in the use of the APL valve, it is desirable that the pressure adjustment of the valve be more sensitive at the lower ranges of pressures than at the higher range and it would therefore be advantageous that the valve have a more precise control of the spring bias at those lower pressures and a lesser degree of control at the higher pressures.

SUMMARY OF THE INVENTION

The adjustable pressure limiting valve of the present invention overcomes the aforesaid difficulties by providing a valve wherein the force exerted by the spring against the movable valve member is adjustable in a non-linear manner as the rotatable control knob is rotated by the user.

The present APL valve includes a spring biasing assembly that can be adjusted by the user by the rotation of a control knob, as in the prior art, however, the resolution between the rotation of the control knob and the force exerted by the spring against the movable valve member varies so that at low patient breathing circuit pressures and set pressures, there is a high resolution and rotating the knob results in a fine tuning and yet the higher pressure relief settings, that same degree of rotation results in more gross changes in the spring force against the movable valve member.

Accordingly, the resolution of the angular rotation of the control knob vs. the amount of spring pressure changes, and, of course, the set relief pressure that opens the APL valve, is a non-linear function and, in fact, can be designed into the operation of the spring biasing assembly to any particular resolution desired by the user depending on the usage of the valve itself.

BRIEF DESCRIPTION OF THE DRAWINGS

FIG. 3 is an exploded view of the valve constructed in accordance with the present invention; and FIG. 4 is a cutaway isomeric view of the present valve.

DETAILED DESCRIPTION OF THE INVENTION

Figure 1:
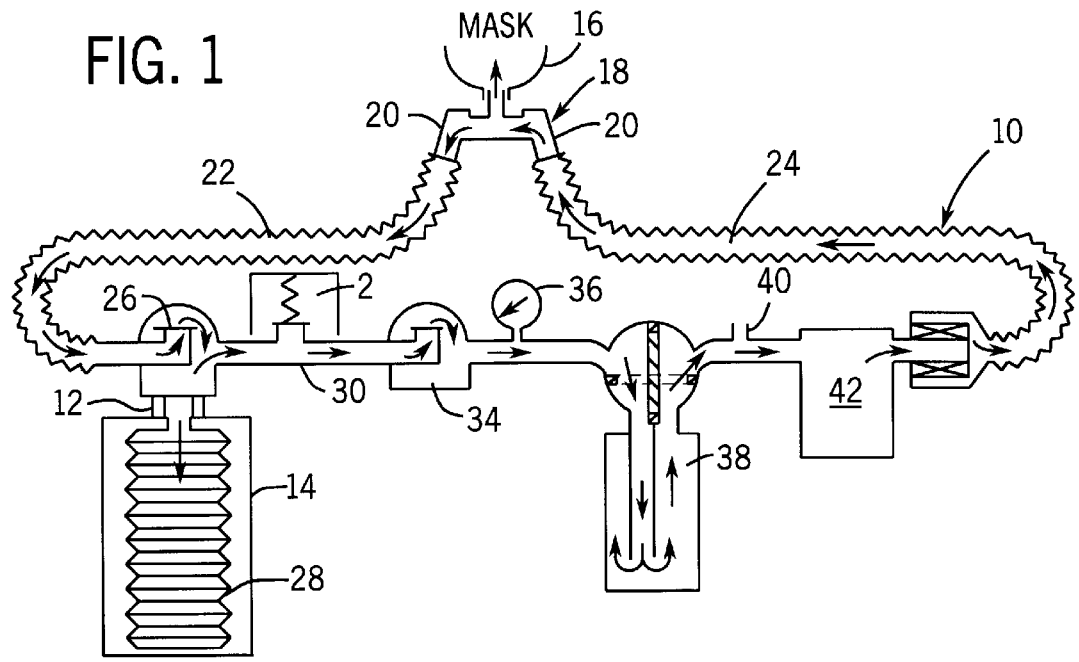
FIG. 1 is a schematic view or a typical patient breathing circuit in which the present valve can be used.

Referring now to FIG. 1, there is shown a schematic view of an anesthesia breathing circuit 10 in which the adjustable pressure limiting (APL) valve 12 of the present invention is utilized. In the further description, the APL valve 12 will be explained with respect to the use of a ventilator (not shown), however, as will be later detailed, the APL valve 12 of the present invention may readily be used where a hand operated collapsible bag is used to breathe the patient.

In the patient breathing circuit 10, as shown, the normal components include a face mask 16 (or endotracheal tube) to communicate with the patient. A wye connector 18 is attached to the mask 16 and provides two tube elements 20 for connection to a pair of conduits 22 and 24. As indicate by the arrows, conduit 22 receives the exhaled breath form the patient and connects to the bellows 28 contained within a bellows container 14 through a check valve 26. The bellows 28 thus receives the exhaled breath from the patient and when the bellows 28 moves upwardly, forces that gas further through the patient breathing circuit 10, ultimately to the patient. The means for operating the bellows 28 is generally a ventilator that pressurizes the space within the bellows container 14 to force the bellows 28 to collapse forcing the gas contained within the bellows into the patient breathing circuit 10.

When the bellows 28 thereafter drops, the system is in the exhalation phase and the exhaled breath is exiting the patient. Following through the patient breathing circuit 10, the gas forced from the bellows 28 is passed through the conduit 30 inasmuch as the check valve 26 prevents the gas from being forced backwardly through conduit 22. The APL valve 12 is biased to a set maximum pressure within the patient breathing circuit 10 and opens to relieve the pressure in the patient breathing circuit 10 whenever the predetermined maximum pressure is exceeded. An exhalation check valve 34 is present in conduit 30 to maintain unidirectional flow and prevent exhalation gases from passing back through the patient breathing circuit 10. A pressure gauge 36 may be included to read pressure within that patient breathing circuit 10. A $CO_2$ absorber 38 in conduit 30 serves to absorb $CO_2$ from the exhalation gases and may be of conventional design having an absorbent material such as soda-lime.

An inlet 40 is provided to introduce fresh gases such as oxygen, nitrous oxide, and the like to the patient breathing circuit 10. The gas flow may then pass through a vaporizer 42 where anesthetic vapors, as desired, are picked up by the gas flow for anesthetizing the patient through conduit 24.

The patient breathing circuit 10 shown, indicates the location and intended function of the APL valve 12 and it is understood that some of the individual components may be used in other locations in the patient breathing circuit 10 or one or more eliminated completely.

Figure 2:
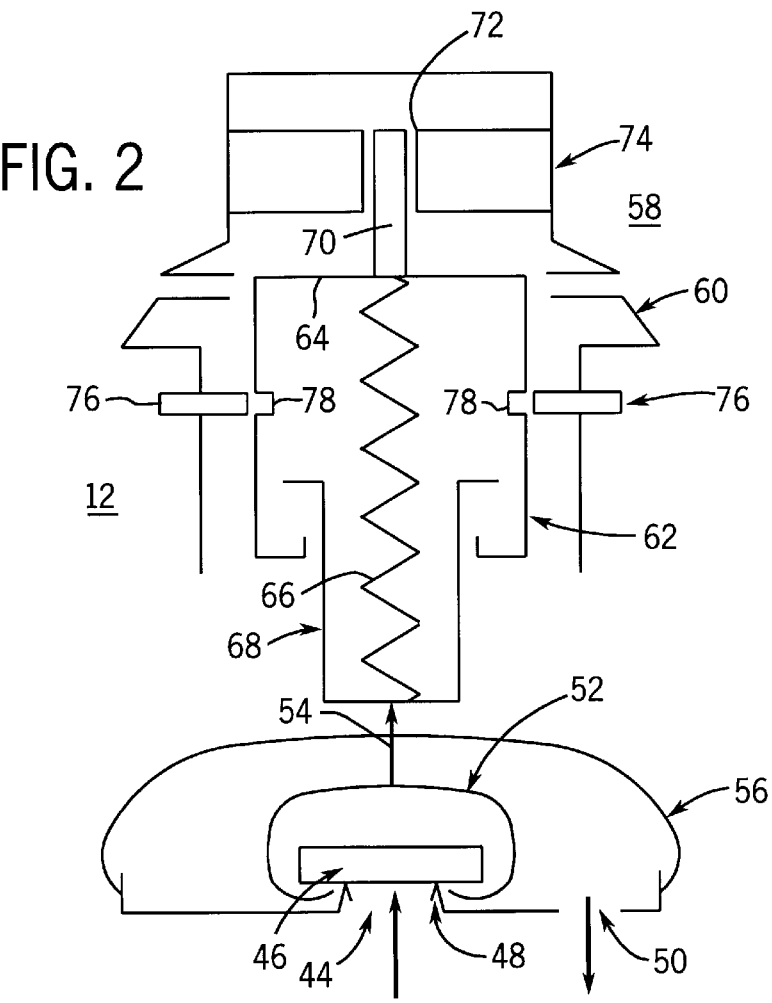
FIG. 2 is a schematic view of a valve constructed in accordance with the present invention.

Turning now to FIG. 2, there is shown a schematic sectional view of the APL valve 12 constructed in accordance with the present invention. As can be seen, the APL valve 12 includes an inlet 44 that communicates with the conduit 30 (FIG. 1) and the internal pressure within the patient breathing circuit 10. Covering the inlet 44 is a movable valve member 46 that is positioned on a valve seat 48 surrounding the inlet 44 and is such that the weight of the movable valve member 46 is sufficient to retain the movable valve member 46 on the valve seat 48. The APL valve 12 includes an outlet 50 that vents the internal pressure of the patient breathing circuit 10 when the APL valve 12 is open. Surrounding the movable valve member 46 is a cage 52, preferable of a molded plastic material, and which has an upstanding hub 54 which may also be molded with the cage 52. A diaphragm 56 may surround the cage 52 and the movable valve member 46 to contain exhaled gases and to prevent those gases from reaching the outside environment. Normally, those gases are directed to a scavenging system to keep those undesirable gases out of the atmosphere surrounding the anesthesia machine. As described, the movable valve member 46 is a relatively simple unit that allows the relief of pressure from within the patient breathing circuit 10 at certain times and at certain pressures.

The pressure at which the APL valve 12 opens is controlled by the force that acts against the movable valve member 46 urging it toward the closed position and, in the present invention, that force is supplied by a spring biasing assembly 58. As will be come apparent, the spring biasing assembly 58 can be used on a variety of movable valve members 46 and is not limited to the present embodiment but can be used where a spring bias is to be exerted on a movable valve member to alter the spring bias as desired to customize the changes in the spring force or spring bias on the movable valve member.

Therefore, the spring biasing assembly 58 comprises a valve body 60 that is fixed with respect to the movable valve member 46 and may be firmly affixed to the particular conduit within the patient breathing circuit 10 where the pressure is being sensed. A cylindrical drum 62 is positioned within the valve body 60 and having an upper surface 64 that provides a seat for spring 66. The other end of the spring 66 is seated in a plunger 68 that is slidably affixed to the cylindrical drum 62. The lower end of plunger 68 contacts the upstanding hub 54 on the cage 52 and therefore, as will be explained, exerts a bias against the movable valve member 46.

At the upper end of the cylindrical drum 62, that is, the end away from the plunger 68, there is a tab 70 that extends upwardly and which fits within a corresponding slot 72 formed in a rotating control knob 74.

To briefly describe the operation of the APL valve 12 therefore, the rotating control knob 74 can be rotated by the user to adjust the bias of the spring 66 against the movable valve member 46 to adjust the maximum pressure that will cause an opening of the APL valve 12 to allow the excess pressure to be released from the patient breathing circuit 10. In carrying out that adjustment of bias, the rotating control knob 74 causes rotation of the cylindrical drum 62. As the cylindrical drum 62 is rotated, guide pins 76 that are fixed to the valve body 60 enter and follow within a helical groove 78 formed in the exterior of the cylindrical drum 62. As the cylindrical drum 62 rotates, therefore, the stationary guide pins 76 are retained within the helical groove 78 and thereby cause the cylindrical drum 62 to move along its central longitudinal axis in a direction toward and away from the movable valve member 46 depending, obviously, on the direction of the rotation.

Accordingly, as the cylindrical drum 62 moves along its longitudinal axis, there is a change in the spring bias against the movable valve member 46 by the compression or decompression of the spring 66 acting against plunger 68, the upstanding hub 54 and, ultimately, the movable valve member 46. As can be seen, therefore, the longitudinal movement of the cylindrical drum 62 depends on the configuration of the helical groove 78 and that helical groove 78 can be customized such that a particular angular rotation of the rotating control knob 74 by the user can have a differing effect on the change of spring bias exerted against the movable valve member 46 and thus the amount of maximum pressure that will open the APL valve 12.

Turning now to FIGS. 3 and 4, there is shown an exploded view and a cutaway isomeric view of the spring biasing assembly 58 constructed in accordance with the present invention. As shown, the spring biasing assembly 58 comprises a valve base 80 (FIG. 4 only) that basically fits over the movable valve member 46 and the valve seat 58 (FIG. 2) and exerts the adjustable bias against the movable valve member toward the closed position to vary the level of pressure required to open the APL valve 12. In FIGS. 3 and 4, therefore the valve body 60 interfits with the valve base 80 and contains the functioning elements of the overall APL valve 12. Cylindrical drum 62 is contained within the valve body 60 and has an upstanding flat tab 70 that is fitted within the rotating control knob 74 so that both elements rotate together, the tab 70, however, also being movable laterally or along the central axis of the cylindrical drum 62. At the lower end of the cylindrical drum 62, the plunger 68 is fitted so as to be slidably engaged in the cylindrical drum 62 with the spring 66 intermediate thereto. The spring 66 is seated against the upper internal surface of the cylindrical drum 62 and against the internal lower surface of the plunger 68 so as to bias those components apart. As noted, the lower external surface of the plunger 68 operates to provide the bias against the movable valve member 46 (FIG. 2).

A helical groove 78 is formed in the external surface of the cylindrical drum 62 and the configuration of the helical groove 78 may vary depending on the relationship between the rotation of the rotatable control knob 74 and the bias that is applied against the movable valve member 46. A pair of guide pins 76 are positioned so as to be fixed with respect to the valve body 60 and which protrude inwardly to enter into the helical groove 78 and travel therein. Accordingly, as the cylindrical drum 62 rotates, it also travels along its longitudinal axis at a rate that is dependent upon the configuration of the helical groove 78.

As can be therefore seen, by determining the configuration of the helical groove 78, the user can determine how much change of bias is applied against the movable valve member 46 as the rotatable control knob 74 is rotated. As in the present application, where a precise and tight resolution is desired at the lower relief pressures, the helical groove 78 may have a tighter pitch at the end toward the movable valve member 46 and a wider pitch at the extreme end away from the movable valve member 46. Thus at the lower pressures, the user can rotate the rotatable control knob 74 and obtain a very fine adjustment of the bias against the movable valve member 46, while at higher pressures within the patient breathing circuit, the user may rotate the rotatable knob 74 with the same angular degrees of rotation but achieve a much larger change in the bias against the movable valve member.

Thus, by a design of the configuration of the helical groove 78, a non-linear relationship can be achieved and individually crafted to achieve a varied change in the opening pressure of the APL valve 12 for the same angular rotation of the rotatable control knob 74.

While the present invention has been set forth in terms of a specific embodiment, it will be understood that the present adjustable pressure limiting valve herein disclosed may be modified or altered by those skilled in the art to other configurations. Accordingly, the invention is to be broadly construed and limited only by the scope and spirit of he claims appended hereto.

I claim:

1. An adjustable pressure limiting valve, the valve comprising:

a body having an inlet and an outlet and a passageway extending therebetween;

a valve seat positioned at the inlet of the body;

a movable valve member adapted to move with respect to the valve seat between an open position wherein the passageway is open and a closed position wherein the passageway is closed;

a biasing means positioned to provide an adjustable bias force on the movable member toward the closed position, the biasing means including a control knob operable by a user by rotation;

a cylindrical drum adapted to rotate with the control knob, the cylindrical drum having an external surface having a helical groove formed therein; and a pin means fixed to the valve body and adapted to be received within the helical groove formed on the cylindrical drum such that the cylindrical drum and pin means translate the rotational movement of the control knob into longitudinal movement of the cylindrical drum toward and away from the movable valve member;

wherein the relationship between the rotational movement of the control knob and the longitudinal movement of the cylindrical drum is non-linear such that the relationship between the rotational movement of the control knob and the change in the bias force on the movable member is also non-linear.

2. The adjustable pressure limiting valve as defined in claim 1 wherein the biasing means comprises a spring.

3. The adjustable pressure limiting valve as defined in claim 1 wherein the cylindrical drum has a first end positioned toward the movable valve member and an opposed, second end, wherein the helical groove formed on the external surface of the cylindrical drum has a non-uniform pitch along the external surface of the cylindrical drum from the first end to the second end.

4. The adjustable pressure limiting valve as defined in claim 3 wherein the pitch of the helical groove is tighter at the first end than at the second end of the cylindrical drum.

5. An adjustable pressure limiting valve, the valve comprising:

a body having an inlet and an outlet and a passageway formed therebetween;

a valve seat formed at the inlet of the valve body;

a movable valve member adapted to move with respect to the valve seat between an open position wherein the passageway is open and a closed position wherein the passageway is closed;

a cylindrical drum contained within the valve body and being movable along the longitudinal axis of the valve body, the cylindrical drum including a helical groove formed along an exterior surface of the cylindrical drum;

a rotatable control knob for rotation by a user, the rotatable control knob being coupled to the cylindrical drum to rotate therewith;

a spring positioned within the valve body between the cylindrical drum and the movable valve member, the spring exerting an adjustable bias force on the valve member toward the closed position;

a guide pin fixed to the valve body and received within the helical groove formed on the cylindrical drum such that rotation of the cylindrical drum causes the cylindrical drum to move along its longitudinal axis to adjust the bias force exerted against the movable valve member, wherein the helical groove is configured to cause a non-linear relationship to exist between the rotational movement of the cylindrical drum and the longitudinal movement of the cylindrical drum.

6. The adjustable pressure limiting valve as defined in claim 5 wherein the helical groove has a non-uniform pitch.

7. The adjustable pressure limiting valve as defined in claim 5 wherein the cylindrical drum includes a first end positioned toward the movable valve member and a second end, the helical groove formed on the exterior surface of the cylindrical drum extending between the first end and the second end, wherein the pitch of the helical groove changes from the first end to the second end.

8. The adjustable pressure limiting valve as defined in claim 7 wherein the pitch of the helical groove increases from the first end of the cylindrical drum to the second of the cylindrical drum.

* * * * *